US010908104B2

(12) United States Patent
Nakayama et al.

(10) Patent No.: US 10,908,104 B2
(45) Date of Patent: Feb. 2, 2021

(54) RADIATION ANALYSIS APPARATUS

(71) Applicant: Hitachi High-Tech Science Corporation, Tokyo (JP)

(72) Inventors: Satoshi Nakayama, Tokyo (JP); Keiichi Tanaka, Tokyo (JP); Atsushi Nagata, Tokyo (JP); Kazuo Chinone, Tokyo (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 189 days.

(21) Appl. No.: 16/041,905

(22) Filed: Jul. 23, 2018

(65) Prior Publication Data
US 2019/0033237 A1  Jan. 31, 2019

(30) Foreign Application Priority Data
Jul. 25, 2017 (JP) ................................ 2017-143653

(51) Int. Cl.
*G01N 23/2252* (2018.01)
*G01T 1/17* (2006.01)
(Continued)

(52) U.S. Cl.
CPC ....... *G01N 23/2252* (2013.01); *A61B 6/4241* (2013.01); *G01N 23/223* (2013.01);
(Continued)

(58) Field of Classification Search
CPC .... G01N 23/2252; G01N 23/223; G01T 1/17; G01T 1/1606; G01T 7/005; H01J 37/023;
(Continued)

(56) References Cited

U.S. PATENT DOCUMENTS

| 3,945,023 A | * | 3/1976 | Stauffer | ................... | G02B 7/30 |
| | | | | | 396/125 |
| 4,687,917 A | * | 8/1987 | Kusaka | .................. | G02B 7/346 |
| | | | | | 250/201.8 |

(Continued)

FOREIGN PATENT DOCUMENTS

JP  2011-039053 A  2/2011

*Primary Examiner* — David P Porta
*Assistant Examiner* — Jeremy S Valentiner
(74) *Attorney, Agent, or Firm* — Banner & Witcoff, Ltd.

(57) ABSTRACT

A radiation analysis apparatus includes an excitation source unit irradiating an object, for which the radiation analysis apparatus analyzes property or a structure, with a first radiation, a radiation detection unit including three or more radiation detectors that detect a second radiation generated from the object irradiated with the first radiation, a radiation focusing unit disposed between the object and the radiation detection unit, and focusing the second radiation, a position changing unit changing a relative positional relationship between the radiation focusing unit and the radiation detection unit, and a control unit controlling the position changing unit to change the positional relationship, based on first information which is stored in a storage unit and indicates an intensity distribution of the second radiation emitted from the radiation focusing unit and second information indicating a distribution based on a detection count of the second radiation detected by each of the radiation detectors.

7 Claims, 7 Drawing Sheets

(51) Int. Cl.
  *H01J 37/02* (2006.01)
  *H01J 37/26* (2006.01)
  *G01T 7/00* (2006.01)
  *G01T 1/16* (2006.01)
  *A61B 6/00* (2006.01)
  *G01N 23/223* (2006.01)

(52) U.S. Cl.
  CPC ............. *G01T 1/1606* (2013.01); *G01T 1/17* (2013.01); *G01T 7/005* (2013.01); *H01J 37/023* (2013.01); *H01J 37/265* (2013.01); *G01N 2223/076* (2013.01); *H01J 2237/0245* (2013.01)

(58) Field of Classification Search
  CPC ............ H01J 37/265; H01J 2237/0245; A61B 6/4241
  See application file for complete search history.

(56) References Cited

U.S. PATENT DOCUMENTS

| | | | |
|---|---|---|---|
| 5,398,273 A * | 3/1995 | Jordan | G01B 15/06 378/145 |
| 2011/0064191 A1 | 3/2011 | Toth et al. | |
| 2015/0119704 A1 * | 4/2015 | Roth | A61B 6/4258 600/425 |
| 2015/0177167 A1 * | 6/2015 | Tanaka | G01N 23/20091 378/49 |
| 2015/0318144 A1 * | 11/2015 | Anan | G01N 23/2252 250/306 |

* cited by examiner

RADIATION ANALYSIS APPARATUS

CROSS-REFERENCE TO RELATED APPLICATION

This application claims priority from Japanese Patent Application No. 2017-143653, filed on Jul. 25, 2017, the entire subject matters of which is incorporated herein by reference.

BACKGROUND

1. Field of the Invention

The present disclosure relates to a radiation analysis apparatus.

2. Background Art

Research and development on techniques of irradiating an object with radiation to analyze properties and a structure of the object have been conducted.

In this regard, a microcalorimeter-type energy dispersive x-ray spectrometer has been known which includes a glass capillary bundle type X-ray lens and a plurality of detectors for detecting X-rays and improves X-ray detection efficiency (See JP-A-2011-39053).

However, in such a microcalorimeter type energy dispersive X-ray spectrometer, in order to change a positional relationship between the X-ray lens and the detectors, a user should change the positional relationship manually. Therefore, unless the user is skilled in the operation of changing the positional relationship, it may be difficult for the user to change the positional relationship to a desired positional relationship. As a result, in the microcalorimeter type energy dispersive X-ray spectrometer, it may be difficult to further improve X-ray detection efficiency by the plurality of detectors.

SUMMARY

An object of the present disclosure is to provide a radiation analysis apparatus capable of easily improving detection efficiency of radiation.

According to an exemplary embodiment of the present disclosure, there is provided a radiation analysis apparatus having:

an excitation source unit configured to irradiate an object, for which the radiation analysis apparatus analyzes property or a structure, with a first radiation;

a radiation detection unit including three or more radiation detectors configured to detect a second radiation generated from the object irradiated with the first radiation;

a radiation focusing unit disposed between the object and the radiation detection unit, and configured to focus the second radiation;

a position changing unit configured to change a relative positional relationship between the radiation focusing unit and the radiation detection unit; and a control unit configured to control the position changing unit to change the positional relationship, based on first information which is stored in a storage unit and indicates an intensity distribution of the second radiation emitted from the radiation focusing unit and second information which indicates a distribution based on a detection count of the second radiation detected by each of the radiation detectors.

According to the present disclosure, there can be provided the radiation analysis apparatus capable of easily improving detection efficiency of radiation.

DETAILED DESCRIPTION

Embodiment

Hereinafter, embodiments of the present disclosure will be described with reference to the drawings.

<Configuration of Radiation Analysis Apparatus>

First, a configuration of a radiation analysis apparatus 1 will be described.

Figure 1:
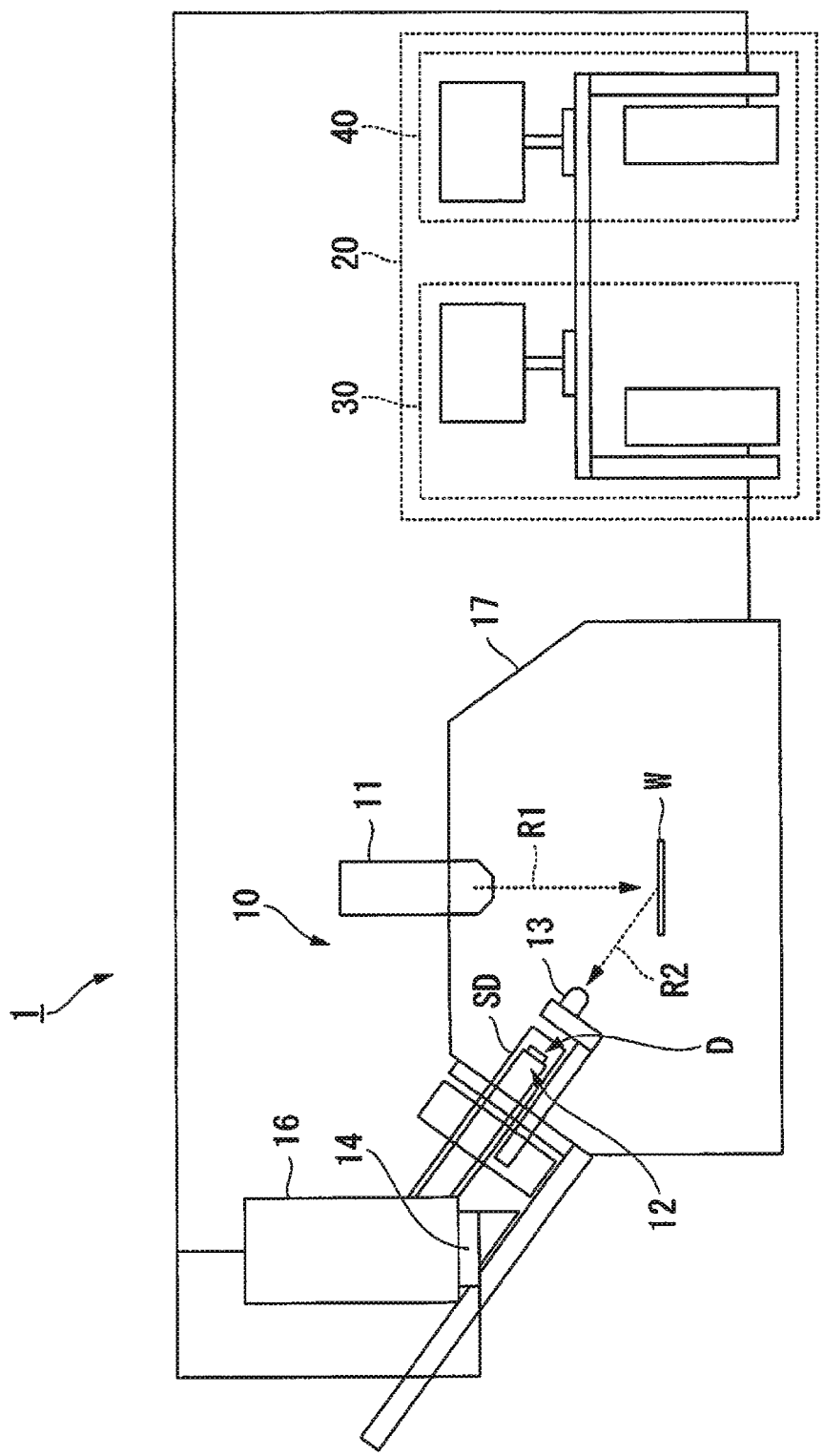
FIG. 1 is a view illustrating an example of a configuration of a radiation analysis apparatus according to an embodiment.

FIG. 1 is a view illustrating an example of a configuration of the radiation analysis apparatus 1 according to an embodiment.

The radiation analysis apparatus 1 includes a detection device 10 and a control device 20.

The detection device 10 includes an excitation source unit 11, a radiation detection unit 12, a radiation focusing unit 13, a position changing unit 14, a cooling device 16, and a housing 17.

The excitation source unit 11 irradiates an object W, for which the radiation analysis apparatus 1 analyzes property or a structure, with a first radiation RE The excitation source unit 11 is, for example, an electron gun. In this case, the first radiation R1 is an electron beam. The excitation source unit 11 may be a device that irradiates the object W with a radiation different from the electron beams such as X-rays or ion beams as the first radiation R1, instead of the electron gun.

The radiation detection unit 12 includes three or more radiation detectors D.

The radiation detector D detects a second radiation R2 such as fluorescent X-rays generated from the object W irradiated with the first radiation RE The radiation detector D is, for example, a detector including a transition edge sensor (TES). Hereinafter, a case where the second radiation R2 is a characteristic X-ray such as fluorescent X-ray generated from the object W will be described as an example. That is, an example of the radiation analysis apparatus 1 is a superconducting X-ray analysis apparatus. The second radiation R2 may be another radiation instead of the fluorescent X-ray. In addition, the radiation detector D may be any detector such as a superconducting tunnel junction (STJ) type sensor, a silicon semiconductor detector, an X-ray charge coupled device (CCD) camera, and a flat panel detector, instead of the detector including the transition edge sensor, as long as the detector is capable of detecting the second radiation R2.

The radiation detection unit 12 may be configured integrally with each of three or more radiation detectors D. In this case, three or more transition edge sensors in the radiation detection unit 12 configure a portion detecting a radiation, among portions that the radiation detection unit 12 has. The portion is provided singly on the arrangement surface M1 described later.

Here, the transition edge sensor detects the second radiation R2 by resistance change occurring when X-rays are incident. A light reception unit of the transition edge sensor includes an absorber for receiving X-rays and a superconductor in which resistance value changes. A temperature of the superconductor before the X-rays are incident is kept at approximately a critical temperature. Therefore, the superconductor is held in an intermediate state between a superconducting state and a normal conducting state. The resistance value of the superconductor in the intermediate state changes abruptly even when a slight temperature change occurs. The transition edge sensor detects the incidence of X-rays by the change in the resistance value. Specifically, in a case where X-rays have been incident on the absorber of the transition edge sensor, a temperature of the absorber rises and the resistance value of the superconductor changes with the temperature rise of the absorber. At this time, if the resistance value changes abruptly in proportion to energy (that is, a risen temperature of the absorber) of the X-rays incident on the absorber, a resistance change in a case where a temperature change is several mK is, for example, $0.1\Omega$ (ohm)). Using this property, the transition edge sensor detects the energy of the second radiation R2 by a magnitude of the resistance change. In a case where the energy of the incident X-rays is low, there may also be a case where the transition edge sensor detects the energy of the second radiation R2, without using the temperature change of the superconductor due to the incidence of X-rays onto the absorber, using the temperature change of the superconductor due to the incidence of X-rays onto the superconductor. The energy of the second radiation R2 is detected in this manner, the radiation detector D outputs an electric signal proportional to the detected energy to the control device 20, as detection information indicating that the second radiation R2 has been detected. Some or all of the three or more radiation detectors D may have a configuration in which kinds thereof are different from each other, a configuration in which shapes thereof are different from each other, or a configuration in which sizes thereof are different from each other. In addition, a configuration in which the detection information includes a signal indicating another information, in addition to the electric signal indicating that the second radiation R2 has been detected, may be adopted. For example, the radiation detector D includes a calculation unit that calculates a value based on information indicating that the second radiation R2 has been detected, and may be configured to output detection information including the value calculated by the calculation unit to the control device 20. The value is, for example, a peak value of the electric signal or a count that the second radiation R2 has been detected. In addition, the detection information output from a certain radiation detector D may include information indicating a position of the radiation detector D, a detection condition in a detection performed by the radiation detector D, and the like. The electric signal may be an analog signal or a digital signal. In a case where the electric signal is the analog signal, the radiation detector D may be configured to include an analog/digital (A/D) converter.

In addition, the radiation detection unit 12 includes the arrangement surface M1 on which the three or more radiation detectors D are respectively arranged. That is, the three or more radiation detectors D are respectively arranged within the arrangement surface M1. The arrangement surface M1 may be a plane, a curved surface, a surface having a step, or a surface having another shape. Hereinafter, a case where the arrangement surface M1 is the plane will be described as an example.

Figure 2:
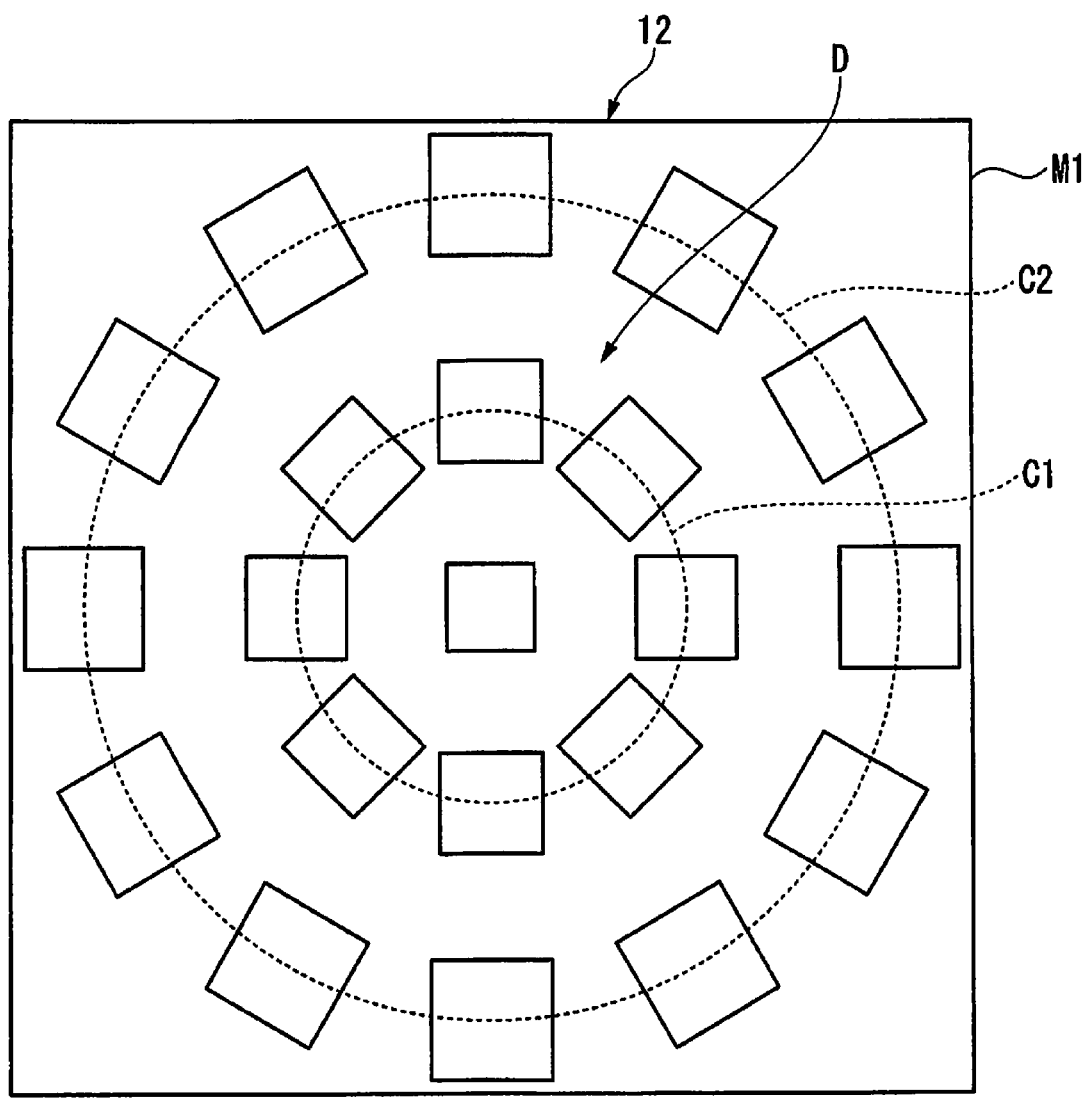
FIG. 2 is a top view illustrating an example of an arrangement surface on which three or more radiation detectors are arranged.

The three or more radiation detectors D are radially arranged within the arrangement surface M1 from the center of the arrangement surface M1, in a case where the three or more radiation detectors D are viewed along a direction perpendicular to the arrangement surface M1. An example of the arrangement of the radiation detectors D in the arrangement surface M1 will be described with reference to FIG. 2. FIG. 2 is a top view illustrating an example of the arrangement surface M1 on which the three or more radiation detectors D are arranged. Since a shape of each of the three or more radiation detectors D is represented by a quadrangle in FIG. 2, in order to simplify the drawing, the radiation detector may have another shape, instead of the quadrangle.

In the example illustrated in FIG. 2, the number of radiation detectors D arranged on the arrangement surface M1 is 21. The number of the radiation detectors D arranged on the arrangement surface M1 may be less than 21 or more than 21, as long as the number is three or more. In addition, in this example, one of the 21 radiation detectors D is arranged at the center position of the arrangement surface M1. Then, eight radiation detectors D are arranged at regular intervals on a first circle C1 having a first radius centered on the position. In addition, 12 radiation detectors D are arranged at equal intervals on a second circle C2 having a second radius centered on the position. Here, the second radius is a radius larger than the first radius. Hereinafter, a case where 21 radiation detectors D are arranged within the arrangement surface M1 in the same manner as the arrangement of FIG. 2 that is the arrangement of the radiation detectors D within the arrangement surface M1 will be described as an example. The arrangement of FIG. 2 that is the arrangement of the radiation detectors D within the arrangement surface M1 is merely an example. For example, the 21 radiation detectors D may be configured to be arranged in a matrix form in the arrangement surface M1 or may be configured to be arranged so as to have another shape within the arrangement surface M1. However, it is preferable that the interval between the radiation detectors D arranged in the arrangement surface M1 is small, in order to prevent the detection efficiency of the radiation detection unit 12 for the second radiation R2 from being lowered. Therefore, in the example illustrated in FIG. 2, the size of each radiation detector D is determined according to a distance from the center position of the arrangement surface M1, and increases as the distance increases. The sizes of respective radiation detectors D may be the same as each other.

Descriptions will be made by returning to FIG. 1. In a case where the radiation detection unit 12 is the transition edge sensor or the STJ type sensor, the radiation detection unit 12 is disposed inside a thermal shield SD. The thermal shield SD which is one of the shield cover shields radiant heat from an outside of the thermal shield SD with a multilayer heat insulator, a vacuum layer, or the like to prevent a temperature inside the thermal shield SD from rising. That is, the thermal shield SD prevents the temperature of the radiation detection unit 12 from rising due to the radiant heat. Accordingly, the superconducting state of the transition edge sensor that the radiation detection unit 12 includes is held until X-rays are incident on the transition edge sensor.

In a case where the radiation detection unit 12 is a silicon semiconductor detector, an X-ray CCD, or the like, the thermal shield SD is configured to hold an operating environment of the radiation detection unit 12 by setting the inside of the shield cover (for example, the thermal shield SD) to vacuum or a nitrogen gas atmosphere.

The radiation focusing unit 13 is an optical member that focuses (concentrates light) the second radiation R2 generated from the object which is irradiated with the first radiation R1 on the radiation detection unit 12. More specifically, the radiation focusing unit 13 focuses the second radiation R2 so as to have a predetermined focal diameter at a predetermined focal length. The radiation focusing unit 13 is, for example, a polycapillary of capillary bundle type or the like. The radiation focusing unit 13 may be another optical member such as a lens that focuses (concentrates light) the second radiation R2 to the radiation detection unit 12, instead of the polycapillary. The radiation focusing unit 13 is disposed between the object that the excitation source unit 11 irradiates with the first radiation R1 and the radiation detection unit 12.

The cooling device 16 is connected to the thermal shield SD and cools the inside of the thermal shield SD. Accordingly, the cooling device 16 can make a state of the transition edge sensor included in the radiation detection unit 12 disposed inside the thermal shield SD to be the superconducting state.

The position changing unit 14 changes the relative positional relationship between the radiation detection unit 12 and the radiation focusing unit 13, based on a control signal acquired from the control device 20.

The position changing unit 14 is provided outside the cooling device 16 and changes a position of the cooling device 16 manually or electrically, thereby changing a position of the radiation detection unit 12. Therefore, it is possible to change the relative positional relationship between the radiation focusing unit 13 and the radiation detection unit 12.

The position changing unit 14 is provided, for example, in the cooling device 16, and may change the position of the radiation detection unit 12 provided inside the thermal shield SD. In addition, the position changing unit 14 may be configured to be capable of relatively moving the radiation focusing unit 13 with respect to the radiation detection unit 12, by being partially or entirely provided on a side of the radiation focusing unit 13. In addition, the position changing unit 14 can move both the radiation focusing unit 13 and the radiation detection unit 12, and may be configured to be capable of changing the relative positional relationship between the radiation focusing unit 13 and the radiation detection unit 12.

It is preferable that the relative positional relationship between the radiation focusing unit 13 and the radiation detection unit 12 is changed in three axes of the XYZ axes, or in four or five axes including tilt or rotation.

The housing 17 is a housing of the detection device 10. In an example thereof, in an inside of the housing 17, an irradiation port through which the excitation source unit 11 performs irradiation with the first radiation R1, an object which is irradiated with the first radiation R1 by the excitation source unit 11, the radiation focusing unit 13, a part or the entirety of the position changing unit 14, and the radiation detection unit 12 disposed inside the thermal shield SD are arranged. In the example illustrated in FIG. 1, in the inside of the housing 17, the object W is disposed as the object which irradiated with the first radiation R1. The object W may be any object as long as it is a sample of a desired object for which a user of the radiation analysis apparatus 1 wishes to analyze property or a structure. A configuration in which, in the inside of the housing 17, the position changing portion 14 is disposed in addition to these, may be adopted. A configuration in which a state of the inside of the housing 17 becomes a vacuum state by a vacuum pump (not illustrated) may be adopted.

The detection device 10 is communicably connected to the control device 20 by a cable. Accordingly, each of the excitation source unit 11, radiation detection unit 12, and the cooling device 16 which are included in the detection device 10 performs an operation based on a control signal acquired from the control device 20. Wired communication via a cable is performed in accordance with standards such as Ethernet (registered trademark) or a universal serial bus (USB). In addition, the detection device 10 may be configured to be connected to the control device 20 by wireless communication performed in accordance with the communication standard such as Wi-Fi (registered trademark).

The control device 20 includes a first control device 30 and a second control device 40. In this example, the control device 20 is configured of the first control device 30 and the second control device 40 that is different from the first control device 30; however, instead of this, may be configured of the first control device 30 integrated with the second control device 40 or the second control device 40 integrated with the first control device 30. In this case, the control device 20 has a function of the first control device 30 and a function of the second control device 40.

The first control device 30 is, for example, configured of single or plural devices having information processing functions, such as a desktop personal computer (PC), a note PC, and a workstation. The first control device 30 controls the excitation source unit 11 to perform irradiation with the first radiation R1.

The second control device 40 is, for example, configured of single or plural devices having information processing functions, such as a desktop personal computer (PC), a note PC, and a workstation.

The second control device 40 acquires the aforementioned detection information from each radiation detector D included in the radiation detection unit 12. The second control device 40 analyzes the property or the structure of the object that is irradiated with the first radiation R1, based on the acquired detection information. The cooling device 16 cools the inside of the thermal shield SD by a cooling control device not illustrated.

<Outline of Radiation Analysis Device>

Here, an outline of the radiation analysis apparatus 1 will be described.

In a radiation analysis apparatus X (for example, a radiation analysis apparatus of the related art) different from the radiation analysis apparatus 1, in a case of changing a positional relationship between capillary and a detector, a user should change the positional relationship manually. Unless the user is skilled in an operation of changing the positional relationship, there may be a case where it is difficult to change the positional relationship to be a positional relationship that the user desires. As a result, in the radiation analysis apparatus X, there may be a case where it is difficult to improve X-ray detection efficiency by the detector.

Therefore, the radiation analysis apparatus 1 irradiates the object W with the first radiation R1, detects the second radiation R2 generated from the object W irradiated with the first radiation R1, by the radiation detectors D, and controls the position changing unit 14 to change the relative positional relationship between the radiation focusing unit 13 and the radiation detection unit 12, based on the first information which is stored in advance and indicates the intensity distribution of the focus of the radiation focusing unit 13 and the second information which indicates a distribution based on a count that each of the radiation detectors D has detected the second radiation R2. Accordingly, the radiation analysis apparatus 1 can easily improve the detection efficiency of radiation. After causing the position changing unit 14 to change the positional relationship, the radiation analysis apparatus 1 irradiates the object W with the first radiation R1, detects the second radiation R2 generated from the object W irradiated with the first radiation R1, by the radiation detectors D, and analyzes the property or the structure of the object W irradiated with the first radiation R1, based on the count that each of the radiation detectors D has detected the second radiation R2. Therefore, the radiation analysis apparatus 1 may be configured to irradiate an object (for example, standard sample or the like) different from the object W with the first radiation R1, detect the second radiation R2 generated from the object irradiated with the first radiation R1, by the radiation detectors D, and control the position changing unit 14 to change the relative positional relationship between the radiation focusing unit 13 and the radiation detection unit 12, based on the first information which is stored in advance and indicates the intensity distribution of the focus of the radiation focusing unit 13 and the second information which indicates a distribution based on the count that each of the radiation detectors D has detected the second radiation R2. In this case, in order to analyze the property or the structure of the object W, the radiation analysis apparatus 1 changes the positional relationship, and then the object is detached therefrom and the object W is attached thereto instead of the object.

Hereinafter, processing that the second control device 40 drives the position changing unit 14 to change the relative positional relationship between the radiation focusing unit 13 and the radiation detection unit 12 will be described in detail.

<Functional Configuration of First Control Device and Second Control Device>

Figure 3:
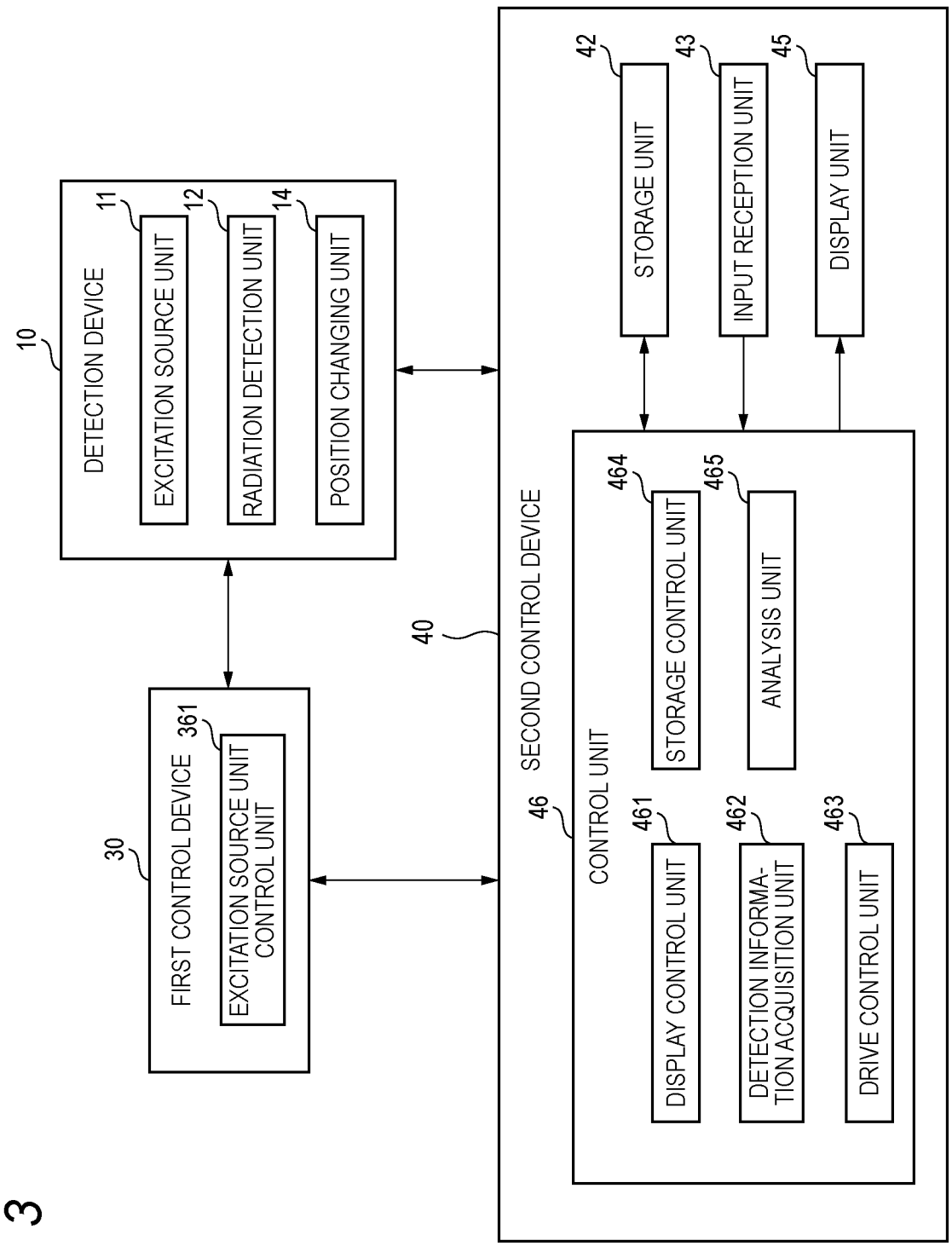
FIG. 3 is a diagram illustrating an example of a functional configuration of a first control device and a second control device.

Hereinafter, a functional configuration of the first control device 30 and the second control device 40 will be described with reference to FIG. 3. FIG. 3 is a diagram illustrating an example of the functional configuration of the first control device 30 and the second control device 40.

The first control device 30 includes an excitation source unit control unit 361.

The excitation source unit control unit 361 is realized by executing various programs stored in a storage unit (not illustrated) such as a hard disk drive (HDD) and a solid state drive (SDD) by a CPU (not illustrated).

The excitation source unit control unit 361 controls the excitation source unit 11 to perform irradiation with the first radiation R1, based on an operation received from a user of the radiation analysis apparatus 1 or a requirement from the second control device 40.

The second control device 40 includes a storage unit 42 which is an HDD or an SDD, an input reception unit 43 which is an input device such as a keyboard or a mouse, a display unit 45 which is a liquid crystal display panel or an organic electro luminescence (EL) display panel, and a control unit 46.

The control unit 46 controls the whole of the second control device 40. The control unit 46 includes a display control unit 461, a detection information acquisition unit 462, a drive control unit 463, a storage control unit 464, and an analysis unit 465. These functional units included in the control unit 46 are realized, for example, by executing various programs stored in the storage unit 42 by a CPU (not illustrated).

The display control unit 461 generates various screens based on the operation received from the user. The display control unit 461 controls the display unit 45 to display the generated screens.

The detection information acquisition unit 462 acquires the detection information from each radiation detector D of the radiation detection unit 12 included in the radiation detection unit 10.

The display control unit 463 drives the position changing unit 14 based on the operation received from the user. In addition, the drive control unit 463 drives the position changing unit 14 based on the detection information stored in the storage unit 42 by the storage control unit 464 described later.

The storage control unit 464 stores the detection information acquired by the detection information acquisition unit 462 on the storage unit 42. In addition, the storage control unit 464 stores an analysis result of the analysis unit 465 on the storage unit 42.

The analysis unit 465 analyzes the property or the structure of the object W based on the acquired detection information and/or the detection information stored in the storage unit 42 by the storage control unit 464.

<Specific Example of Processing that Control Device Performs>

Figure 4:
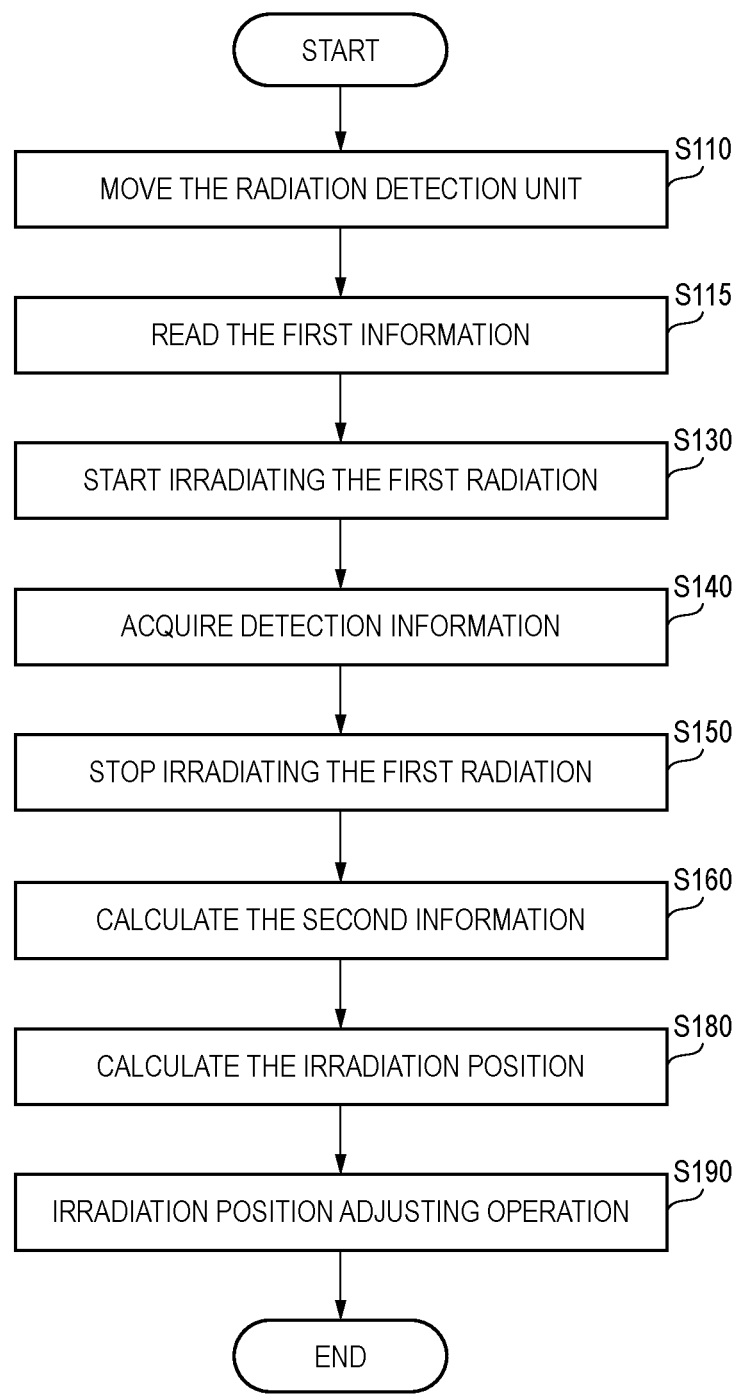
FIG. 4 is a flowchart illustrating an example of a flow of processing that a control device performs.

Hereinafter, a specific example of processing that the control device 20 performs will be described with reference to FIG. 4. FIG. 4 is a flowchart illustrating an example of a flow of processing that a control device 20 performs. Hereinafter, a case where the object W is disposed in advance at a predetermined arrangement position that the excitation source unit 11 irradiates with the first radiation R1, among the inside of the housing 17, will be described.

The drive control unit 463 drives the position changing unit 14, and relatively moves the radiation detection unit 12 with respect to the radiation focusing unit 13. Accordingly, the drive control unit 463 causes the relative positional relationship between the radiation detection unit 12 and the radiation focusing unit 13 to match with the predetermined initial positional relationship (Step S110). Here, the initial positional relationship will be described with reference to FIG. 5.

Figure 5:
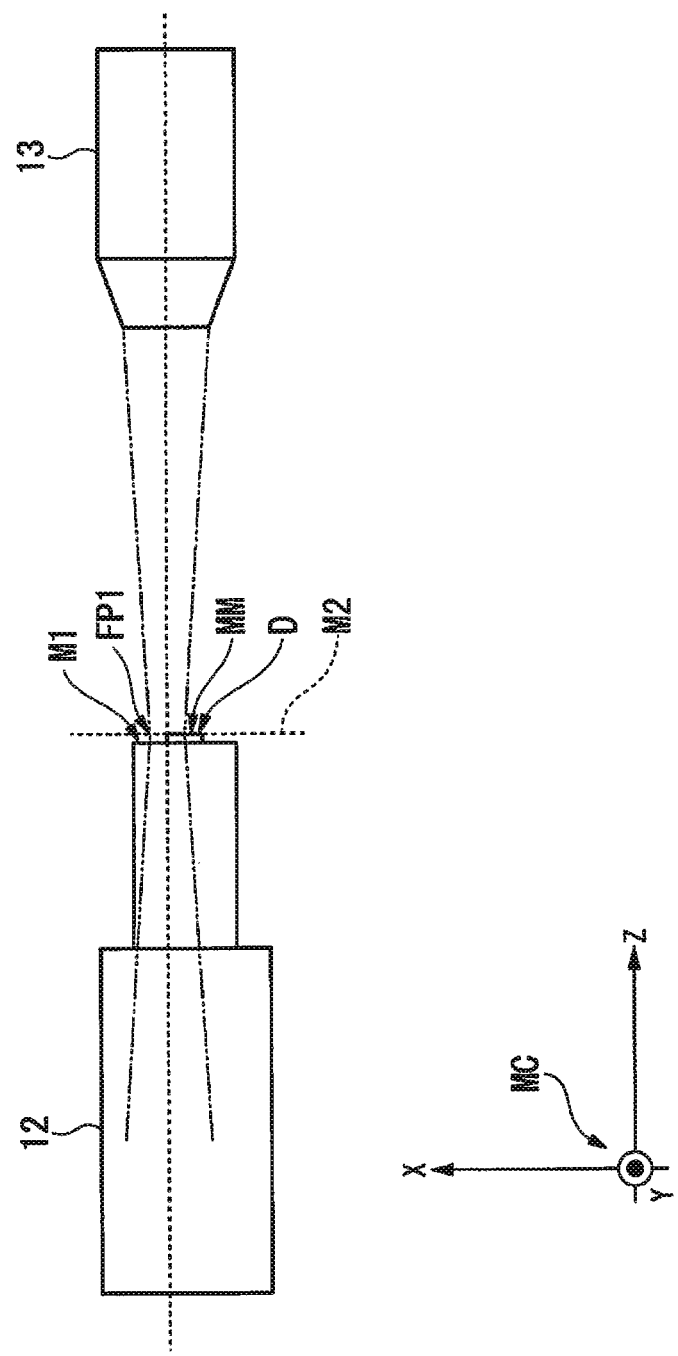
FIG. 5 is a left side view illustrating an example of a radiation detection unit and a radiation focusing unit, in a case where a relative positional relationship between the radiation detection unit and the radiation focusing unit matches an initial positional relationship.

FIG. 5 is a view illustrating an example of the radiation detection unit 12 and the radiation focusing unit 13, in a case where the relative positional relationship between the radiation detection unit 12 and the radiation focusing unit 13 matches the initial positional relationship. The relative positional relationship between the radiation detection unit 12 and the radiation focusing unit 13 illustrated in FIG. 5 is the positional relationship when the radiation detection unit 12 and the radiation focusing unit 13 were viewed from the same direction as the direction in which the radiation analysis apparatus 1 illustrated in FIG. 1 is seen.

In addition, a three-dimensional orthogonal coordinate system MC shown in FIG. 5 is a coordinate system representing the relative positional relationship between the radiation detection unit 12 and the radiation focusing unit 13. In this example, a positive direction of the Z-axis in the three-dimensional orthogonal coordinate system MC matches with a direction from the radiation detection unit 12 to the radiation focusing unit 13, among directions perpendicular to the arrangement surface M1. In this example, the X-axis in the three-dimensional orthogonal coordinate system MC matches with a direction from the bottom to the top of a plane of the paper in FIG. 5. In addition, in this example, the Y-axis in the three-dimensional orthogonal coordinate system MC matches a direction in FIG. 5 that is perpendicular to the plane of the paper and from a back side to a front side of the plane of the paper. That is, in this example, an XY plane extended by the X-axis and the Y-axis in the three-dimensional orthogonal coordinate system MC is a plane parallel to the arrangement surface M1.

The initial positional relationship is, for example, a relative positional relationship between the radiation focusing unit 13 and the radiation detection unit 12 in a case where at least three or more radiation detectors D among the 21 radiation detectors D are included in the irradiation area. The irradiation area is an area which is irradiated with the second radiation R2 focused by the radiation focusing unit 13, among an area within a virtual surface M2 including a surface MM that is a detection surface of each radiation detector D arranged on the arrangement surface M1 (in FIG. 5, an area sandwiched between two two-dot chain lines on the surface). In this example, positions of respective surfaces MM in the three-dimensional orthogonal coordinate system MC in the Z-axis direction are the same, but may be configured to be different from each other. In addition, in this example, the arrangement surface M1 and the surface M2 are parallel, but may be nonparallel. A point FP1 shown in FIG. 5 represents a focus of the second radiation R2 focused by the radiation focusing unit 13. In the example shown in FIG. 5, a position of the point FP1 in the three-dimensional orthogonal coordinate system MC in the Z-axis direction matches with a position of the surface M2 in the Z-axis direction. The position of the point FP1 in the three-dimensional orthogonal coordinate system MC in the Z-axis direction may not match with the position of the surface M2.

After the processing of Step S110 is performed, the drive control unit 463 reads the first information stored in advance in the storage unit 42 from the storage unit 42 (Step S115). The first information indicates the intensity distribution that the user desires. Specifically, the first information is information indicating an intensity distribution of a focus of the radiation focusing unit 13, that is measured in advance, information indicating the intensity distribution corrected by the user of the radiation analysis apparatus 1, information indicating an intensity distribution calculated in advance by theoretical calculation, information indicating an intensity distribution in which each radiation detector D detects the second radiation R2 with a high degree of the detection efficiency, information indicating an intensity distribution in which each radiation detector D detects the second radiation R2 with the highest degree of the detection efficiency, and the like. Hereinafter, a case where the first information is information indicating an intensity distribution of a focus of the radiation focusing unit 13, that is measured in advance.

Figure 6:
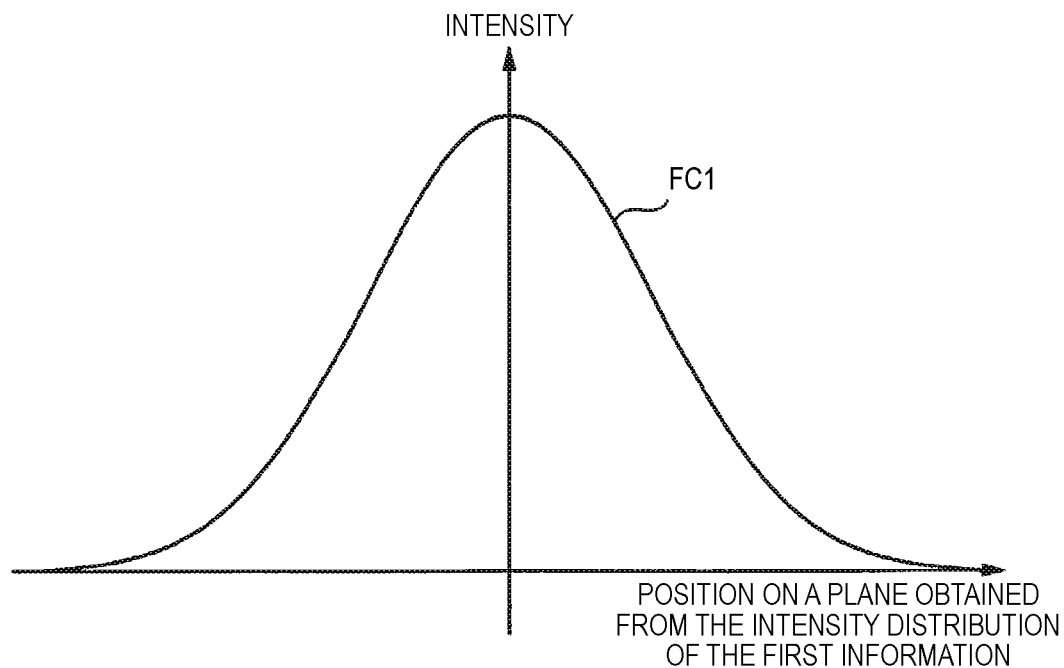
FIG. 6 is a graph illustrating an example of an intensity distribution that first information indicates.

FIG. 6 is a graph illustrating an example of an intensity distribution that the first information indicates. The intensity distribution shown in FIG. 6 is represented by a graph obtained by projecting the intensity distribution of the focus of the radiation focusing unit 13 on a two-dimensional plane, in order to simplify the drawing. A horizontal axis of the graph shown in FIG. 6 indicates a position on a plane obtained from the intensity distribution of the first information which is a position in a direction perpendicular to the central axis of the radiation focusing unit 13. A vertical axis of the graph indicates an intensity of X-rays. A curve FC1 shown in FIG. 6 indicates a function representing the intensity distribution. The first information may also be information provided in advance from a manufacturer (a maker or the like) of the radiation focusing unit 13. The user stores the first information provided by the manufacturer provided by the manufacturer in the storage unit 42 at a timing before the processing of Step S110 starts. The drive control unit 463 may be configured to acquire the first information from a server via a communication network such as the Internet, based on the operation received from the user at the timing. In this case, the storage control unit 464 stores the first information acquired from the server by the drive control unit 463 on the storage unit 42.

Next, the excitation source unit control unit 361 controls the excitation source unit 11 to start irradiating the object W with the first radiation R1 (Step S130). Accordingly, the radiation detector D outputs the detection information to the second control device 40 each time the second radiation R2 is detected. Next, the detection information acquisition unit 462 acquires detection information from each of the radiation detectors D until a predetermined measuring time has elapsed (Step S140). Then, the storage control unit 464 stores the acquired detection information on the storage unit 42. More specifically, in a case where the detection information acquisition unit 462 has acquired detection information from a certain radiation detector D, the storage control unit 464 stores the acquired detection information, a time information indicating the time when the detection information has been acquired, and detector information indicating the radiation detector D by corresponding to one another, on the storage unit 42. The measurement time is, for example, 1 minute. The measurement time may be shorter than 1 minute and may be longer than 1 minute. Next, the excitation source unit control unit 361 controls the excitation source unit 11 to stop the irradiating the object W with the first radiation R1 (Step S150).

Figure 7:
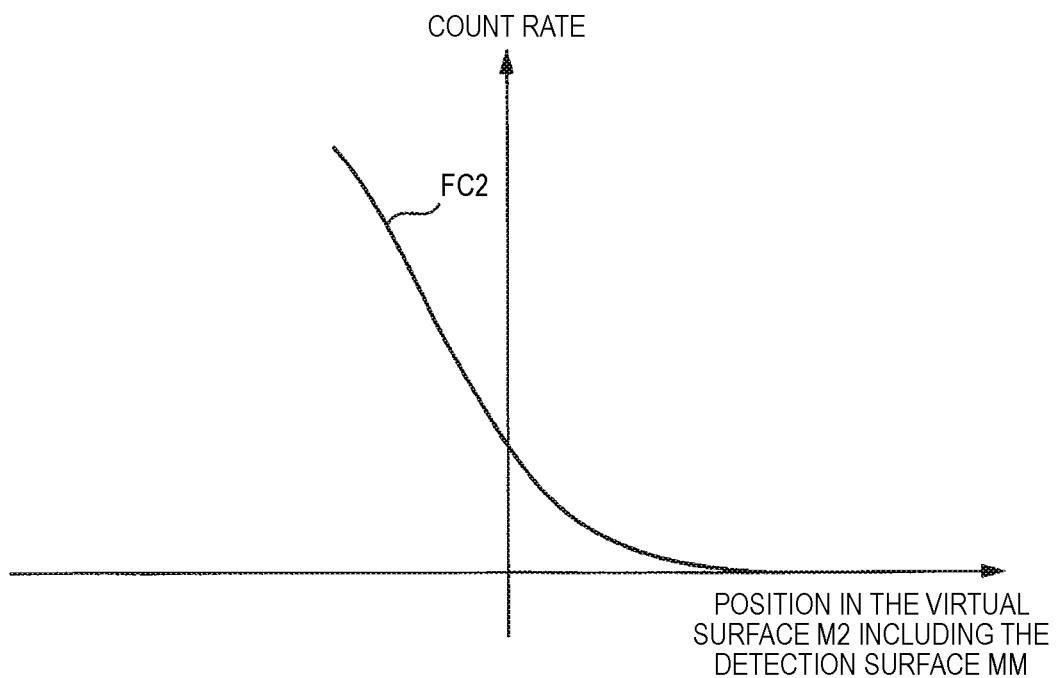
FIG. 7 is a graph illustrating an example of a distribution that second information indicates.

Next, the drive control unit 463 calculates a count rate which is a count that the radiation detector D has detected the second radiation R2 per unit time, for each radiation detector D, based on a plurality of pieces of detection information stored in the storage unit 42 in step S140. The unit time is 1 second, in this example. The unit time may be another time, such as 1 minute. The drive control unit 463 calculates a distribution of the calculated count rate for each radiation detector D as the second information (Step S160). Specifically, the drive control unit 463 generates a histogram that represents a relationship between the position of the radiation detector D and the count rate corresponding to the incident amount of the second radiation R2 on the position per unit time, for each radiation detector D. The drive control unit 463 performs fitting of the generated histogram with a predetermined function, and calculates a fitting curve that is obtained by the fitting, as the second information indicating the distribution of the counting rate for each radiation detector D. Hereinafter, a case where the predetermined function is a Gaussian function will be described as an example. The predetermined function may be another function such as a function based on a polynomial, instead of the Gaussian function. FIG. 7 is a graph illustrating an example of a distribution that second information indicates. The distribution shown in FIG. 7 is represented by a graph obtained by projecting the distribution of the count rate for each radiation detector D on a two-dimensional plane, in order to simplify the graph. A horizontal axis of the graph shown in FIG. 7 indicates a position in the virtual surface M2 including the surface MM that is the detection surface of each radiation detector D arranged on the arrangement surface M1, with the center of the radiation detector D at the center as an origin. In addition, a vertical axis of the graph indicates the count rate. A curve FC2 shown in FIG. 7 indicates a function representing the distribution. Here, the curve FC2 shown in FIG. 7 is a curve having no peak, but this is merely an example, and there may be a case of a curve having a peak.

After the processing of Step S160 is performed, the drive control unit 463 matches the first information read from the storage unit 42 in Step S115 with the second information calculated in Step S160, and calculates a position estimated that there is a peak of a function representing the distribution that the second information indicates, on the XY plane in the three-dimensional orthogonal coordinate system MC, as an irradiation position. (Step S180). That is, in Step S180, the drive control unit 463 calculates a position in the three-dimensional orthogonal coordinate system MC at the center of the irradiation area which is irradiated with the second radiation R2 on the surface M2 during the processing in Step S140, as the irradiation position. Here, the position is a position in the XY plane in the three-dimensional orthogonal coordinate system MC. After the processing of step S180 is performed, the drive control unit 463 drives the position changing unit 14 based on the irradiation position calculated in Step S180, and performs an irradiation position adjusting operation that changes the relative positional relationship between the radiation detection unit 12 and the radiation focusing unit 13 (Step S190). In the irradiation position adjusting operation, the drive control unit 463 calculates a vector indicating a distance and a direction from the irradiation position calculated in Step S180 on the XY plane in the three-dimensional orthogonal coordinate system MC to the position of the peak of the distribution that the first information read in Step S115 indicates. The position indicates a position on a plane obtained from the intensity distribution of the first information, which is a position of the peak in a direction perpendicular to the central axis, based on the central axis of the radiation focusing unit 13. Thus, in the irradiation position adjusting operation, the drive control unit 463 relatively moves the radiation detection unit 12 with respect to the radiation focusing unit 13 by the distance according to the calculated vector, by the position changing unit 14. Accordingly, the radiation analysis apparatus 1 can easily improve the detection efficiency of the radiation detection unit 12 for the second radiation R2. After the processing of Step S190 is performed, the drive control unit 463 ends processing.

The processing from Step S130 to Step S190 may be repeated for the purpose of improving accuracy or combining rough adjustment and fine adjustment.

Therefore, the radiation analysis apparatus 1 controls the position changing unit 14 to change the relative positional relationship between the radiation focusing unit 13 and the radiation detection unit 12, based on the first information which is stored in advance in the storage unit 42 and indicates the intensity distribution of the focus of the radiation focusing unit 13 and the second information which indicates a distribution based on the count that each of the radiation detectors D has detected the second radiation R2. Accordingly, the radiation analysis apparatus 1 can easily improve the detection efficiency of the radiation detection unit 12 for the second radiation R2.

The drive control unit 463 may be configured to change, before and after performing the processing of Step S190 or during the processing, the positional relationship in a direction along the Z-axis in the three-dimensional orthogonal coordinate system MC, among the relative positional relationship between the radiation detection unit 12 and the radiation focusing unit 13, to match a profile of the distribution that the first information indicates and the distribution that the second information indicates. In this case, the drive control unit 463 calculates a movement distance in the direction by a full width at half maximum of the distributions that the first information and the second information respectively indicate, which is the movement distance moved in the direction by the position changing unit 14. Here, the drive control unit 463 calculates the movement direction in a case of being moved by the position changing unit 14 in the positive direction of the Z-axis, as a positive value, and calculates the movement direction in a case of being moved by the position changing unit 14 in a negative direction of the Z-axis, as a negative value. The display control unit 463 drives the position changing unit 14 based on the calculated movement direction to perform moving by the position changing unit 14. Accordingly, the drive control unit 463 changes the positional relationship in the direction along the Z-axis to the positional relationship that the user desires.

Modification Example 1 of Embodiment

Hereinafter, Modification Example 1 of the embodiment will be described. In Modification Example 1 of the embodiment, the same reference numerals are given to the same constituent parts as in the embodiment, and the description thereof will be omitted. In addition, in the following description, the position on the placement surface M1 in the three-dimensional orthogonal coordinate system MC will be referred to simply as the position on the arrangement surface M1, for the convenience of explanation. In the embodiment, 21 radiation detectors D are radially arranged within the arrangement surface M1, from the center of the arrangement surface M1. However, the 21 radiation detectors D arranged on the arrangement surface M1 may be arranged asymmetrically with respect to the rotation about the axis passing through the center of the arrangement surface M1, when viewing the arrangement surface M1 toward the above-described front direction. In this case, a method described in the embodiment, there may be a case where it is difficult to improve the detection efficiency of the radiation detection unit 12. In addition, in the method, even if the 21 radiation detectors D are radially arranged from the center of the arrangement surface M1, in a case where the peak position of the intensity distribution of the first information is adjusted to a position different from the center of the arrangement surface M1, it is difficult to improve the detection efficiency of the radiation detection unit 12. Then, in Modification Example 1 of the embodiment, the drive control unit 463 calculates an irradiation target position which is a target position at which the above-described irradiation position is matched based on the arrangement of the 21 radiation detectors D within the arrangement surface M1 in Step S180 and the first information. Then, the drive control unit 463 operates the position changing unit 14 in Step S190 and controls the position changing unit 14 to change the relative positional relationship between the radiation detection unit 12 and the radiation focusing unit 13 such that the calculated irradiation target position matches with the irradiation position. Accordingly, the radiation analysis apparatus 1 can more reliably improve the detection efficiency of the radiation detection unit 12 for the second radiation R2.

Specifically, the drive control unit 463 performs arrangement matching which is a matching between the intensity distribution that the first information indicates and the arrangement of 21 radiation detectors D on the arrangement surface M1, for each position on the arrangement surface M1, thereby calculating the irradiation target position. In the arrangement matching performed for a certain position on the arrangement surface M1, a position on the XY plane (that is, a plane formed by two horizontal axes in the intensity distribution) in the intensity distribution is associated with a position on the arrangement surface M1, such that the position matches with the position of the peak of the intensity distribution that the first information indicates.

Figure 8:
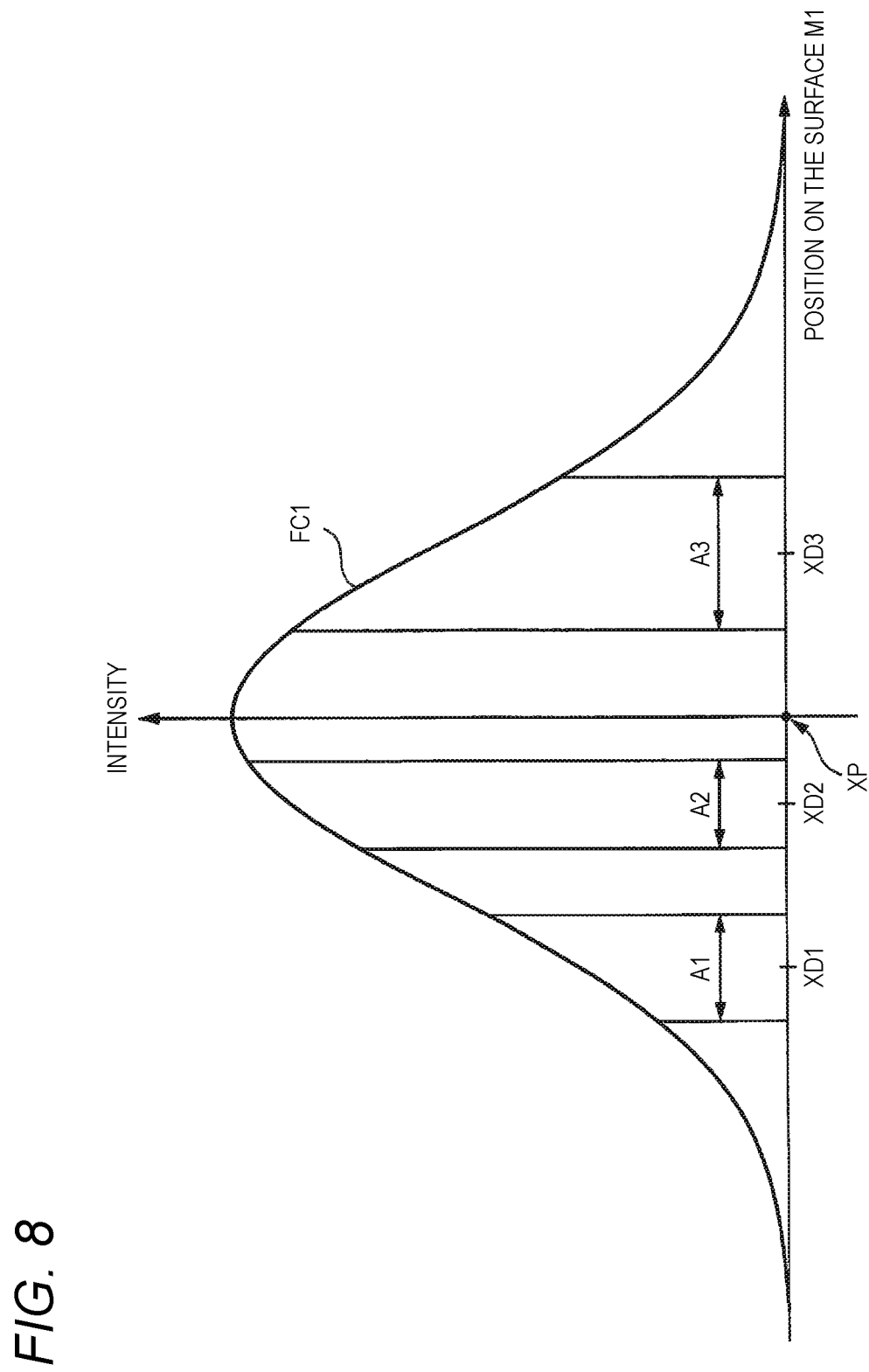
FIG. 8 is a graph illustrating an example of an intensity distribution that the first information indicates, after causing an arrangement of 21 radiation detectors on the arrangement surface to match with the intensity distribution that the first information indicates such that a certain position on the arrangement surface matches with a position of a peak of the intensity distribution that the first information indicates.

FIG. 8 is a graph illustrating an example of the intensity distribution that the first information indicates, after causing the arrangement of the 21 radiation detectors D on the arrangement surface M1 to match with the intensity distribution that the first information indicates, such that a certain position XP on the arrangement surface M1 matches with a position of a peak of the intensity distribution that the first information indicates. That is, FIG. 8 is a graph illustrating an example of the intensity distribution, that the first information indicates, in which the position on the XY plane is converted into the position on the arrangement surface M1 by the association. The intensity distribution shown in FIG. 8 is represented by a graph obtained by projecting the intensity distribution, that the first information indicates, on a two-dimensional plane, in order to simplify the graph.

In FIG. 8, a case where the radiation detectors D arranged on the arrangement surface M1 are three radiation detectors D of a radiation detector D1, a radiation detector D2, and a radiation detector D3 will be described. A position XD1 shown in FIG. 8 indicates a position of the radiation detector D1 on the arrangement surface M1. A position XD2 shown in FIG. 8 indicates a position of the radiation detector D2 on the arrangement surface M1. In addition, a position XD3 shown in FIG. 8 indicates a position of the radiation detector D3 on the arrangement surface M1. An area A1 shown in FIG. 8 indicates an area occupied by the radiation detector D1 by the size thereof, among an area on the arrangement surface M1. An area A2 shown in FIG. 8 indicates an area occupied by the radiation detector D2 by the size thereof, among the area on the arrangement surface M1. In addition, an area A3 shown in FIG. 8 indicates an area occupied by the radiation detector D3 by the size thereof, among the area on the arrangement surface M1. Each of the areas A1 to A3 is an example of an area for each of the radiation detectors D in the arrangement surface M1.

After performing arrangement matching on a certain position on the arrangement surface M1, the drive control unit 463 reads design information including information indicating the size of each radiation detector D, which is stored in the storage unit 42 in advance, from the storage unit 42. In addition, the drive control unit 463 reads detection sensitivity information indicating detection sensitivity of each radiation detector D, which is stored in advance in the storage unit 42, from the storage unit 42. The drive control unit 463 specifies an area for each radiation detector D, as the areas A1 to A3 shown in FIG. 8, in the intensity distribution that the first information indicates after the arrangement matching was performed on the position, based on the design information read out from the storage unit 42. Then, the drive control unit 463 performs intensity calculation processing of calculating the intensity of the radiation detector D corresponding to the area, for each of the specified areas. Specifically, in the intensity calculation processing, the drive control unit 463 calculates a surface area of a portion, which is surrounded by a certain area among the specified area and a curve (in the example shown in FIG. 8, the curve FC1) of a function representing the intensity distribution that the first information indicates. The drive control unit 463 calculates a value obtained by multiplying the calculated surface area by the detection sensitivity of the radiation detector D corresponding to the area, which is indicated by the detection sensitivity information read from the storage unit 42, as the intensity of the radiation detector D. The drive control unit 463 performs intensity calculation processing of calculating the intensity of the radiation detector D in this manner, for each of radiation detectors D corresponding to each of the specified areas. Then, the drive control unit 463 calculates the sum of the calculated intensities for each radiation detector D.

The drive control unit 463 calculates the sum of the intensities for each radiation detector D, for each piece of the first information obtained by performing the arrangement matching for each position on the arrangement surface M1, that is, for each position on the arrangement surface M1. Then, the drive control unit 463 calculates (specifies) a position on the arrangement surface M1 corresponding to the maximum sum, among the calculated sum for each position on the placement surface M1, as the irradiation target position. In a case where the irradiation target position obtained by being calculated in this manner matches with the irradiation position, the detection efficiency of the radiation detection unit 12 improves as compared with a case where the irradiation target position does not match with the irradiation position.

In addition, as necessary, the drive control unit 463 calculates (specifies), as the irradiation target position, a position corresponding to the sum which the maximum sum within the range satisfying upper limit of set count rate or lower limit of life for the purpose of load distribution and optimization in consideration of the maximum count rate and the life of the detector, according to the maximum coefficient rate of the detector.

When explaining the above-described intensity calculation processing with the Expression, for example, the drive control unit 463 calculates the position on the arrangement surface M1, at which a value of the following expression (1) is the maximum, as the irradiation target position.

$$I = \sum_{Ch=1}^{n} \left( K_{Ch} \int f dA_{Ch} \right) \quad (1)$$

Here, I indicates the sum of the intensities for each radiation detector D, which is calculated based on the first information after the arrangement matching has been performed for a certain position on the arrangement surface M1.

Ch indicates a number for identifying each radiation detector D. n indicates the sum of the radiation detectors D arranged on the arrangement surface M1. KCh indicates the detection sensitivity of the radiation detector D identified by Ch. f indicates a function representing the intensity distribution. ACh indicates an area occupied by the radiation detector D identified by Ch by the size thereof, among the area on the arrangement surface M1.

In this manner, even in a case where the 21 radiation detectors D arranged on the arrangement surface M1 are arranged asymmetrically with respect to the rotation about the axis passing through the center of the arrangement surface M1 when viewing the arrangement surface M1 toward the above-described front direction, the radiation analysis apparatus 1 can improve the detection efficiency of the radiation detection unit 12 for the second radiation R2 by calculating the irradiation target position.

Modification Example 2 of Embodiment

Hereinafter, Modification Example 2 of the embodiment will be described. In Modification Example 2 of the embodiment, the same reference numerals are given to the same constituent parts as in the embodiment, and the description thereof will be omitted. In the embodiment, the drive control unit 463 calculates the second information based on the detection information that the detection information acquisition unit 462 acquires from the radiation detection unit 12 (that is, the radiation detector D). However, instead of this, the drive control unit may be configured to generate information indicating the intensity distribution of the second radiation R2 focused by the radiation focusing unit 13, which is the distribution detected by a second radiation detection unit which is a radiation detection unit different from the radiation detection unit 12, as the second information. In this case, the second radiation detection unit has a detector capable of detecting the intensity distribution such as an X-ray charge coupled device (CCD) camera or flat panel detector. In addition, in this case, the drive control unit 463 reads position information which is information indicating the relative position between the radiation detection unit 12 and the second radiation detection unit, which is stored in advance in the storage unit 42, from the storage unit 42. Then, the drive control unit converts the intensity distribution into the intensity distribution of the second radiation R2 when detecting the second radiation R2 by the radiation detection unit 12, based on the intensity distribution on the detection surface on which the second radiation detection unit detects the second radiation R2 and the read position information, and generates second information indicating the converted intensity distribution.

For example, the second radiation detection unit may be configured to be arranged in a shutter shielding a space between the radiation detector D included in the radiation detection unit 12 and the radiation focusing unit 13. The shutter is configured by a plate member that can be opened and closed, between the radiation detection unit 12 and the radiation focusing unit 13, and opens and closes the plate member in response to a demand from the second control device 40. Accordingly, the radiation analysis apparatus 1 can provide the second radiation detection unit to the detection device 10, without adding a new member for providing the second radiation detection unit.

<Effect Obtain in Embodiment and Reason Thereof>

As an X-ray detector included in an X-ray analysis apparatus capable of discriminating energy of X-rays, an energy dispersive X-ray detector and a wavelength dispersive X-ray detector are known. The energy dispersive X-ray detector converts the energy of X-rays incident into the energy dispersive X-ray detector into an electric signal and calculates the energy by the magnitude of the converted electric signal. On the other hand, the wavelength dispersive X-ray detector spectrally disperses X-rays incident on the wavelength dispersive X-ray detector to be monochromatic, and detects the monochromatic X-rays with a proportional counter.

As the energy dispersive X-ray detector, a silicon lithium type detector, a silicon drift type detector, and a semiconductor detector such as germanium detector are known. For example, the silicon lithium type detector and the silicon drift type detector are frequently used for an elemental analysis apparatus of an electron microscope, and can detect energy of approximately 0 to 20 keV. However, since these detectors use silicon, energy resolution depends on a band gap (1.1 eV) of the silicon, it is difficult to improve the energy resolution to approximately 130 eV or more, and the energy resolution is lower than that of the wavelength dispersive X-ray detector by 10 times or more.

In a case where X-rays are incident on the energy dispersive X-ray detector having the energy resolution of 130 eV, the energy dispersive X-ray detector can detect the energy of the incident X-ray with an error of approximately 130 eV. Accordingly, the smaller the error, the higher the energy resolution.

The superconducting X-ray analysis apparatus described as an example of the radiation analysis apparatus 1 in the embodiment includes the transition edge sensor as described above, as the superconducting X-ray detector. The transition edge sensor is a type of the superconducting X-ray detector known as an energy dispersive X-ray detector having energy resolution equivalent to the energy resolution of the wavelength dispersive X-ray detector. The transition edge sensor is also referred as to a microcalorimeter. As the superconducting X-ray detector, a Josephson tunnel junction element using Josephson effect, a superconducting single photon detector using superconducting line, a superconducting mechanics inductance detector, and the like are known, in addition to the transition edge sensor.

For example, the transition edge sensor has the energy resolution higher than other superconducting X-ray detectors. For example, the energy resolution of the transition edge sensor when detecting characteristic X-ray energy of 5.9 keV can be 10 eV or less.

In a case where the transition edge sensor is attached to a scanning electron microscope having an electron generating source such as a tungsten filament, energy of characteristic X rays generated from an object irradiated with an electron beam is detected by the transition edge sensor, whereby the semiconductor type X-ray conductor can discriminate non-discriminable characteristic X-rays (for example, Si-kα, W-Mα, and β).

As an index showing performance of the X-ray detector, a counting efficiency is known, in addition to the energy resolution described above. The counting efficiency is determined by a surface area, a thickness, or material of the radiation reception unit of the X-ray detector, a distance between a radiation generating source and the X-ray detector, the maximum count rate of the X-ray detector, and the like. For example, a general silicon drift type detector has the surface area of several $mm^2$ to several hundred $mm^2$ and the maximum count rate is several ten thousand cps to several hundred thousand cps. On the other hand, the surface area of the transition edge sensor is smaller than 1 mm$^2$ and the maximum count rate thereof is approximately several hundred cps, in general.

From this, as described in the embodiment, it can be said that it is very important that the radiation analysis apparatus 1 including the transition edge sensor as the superconducting X-ray detector includes the position changing unit 14 and can move the radiation detection unit 12 toward a movement direction that the user desires by the movement amount that the user desires, by the position changing unit 14, from the viewpoint of improving the counting efficiency of the radiation analysis apparatus 1. In a case where the user manually changes the relative position of the radiation detection unit 12 to the radiation focusing unit 13, it is difficult to improve the counting efficiency. Such difficulty is also easily understood from the fact that the second radiation R2 focused by the radiation focusing unit 13 to be 100 μm should be incident on the light reception unit having a surface area smaller than 1 mm$^2$.

The embodiment and modified example of the embodiment described above are applied to the radiation analysis apparatus 1 in a case of performing these processing in advance before analyzing the property or the structure of the object W based on the count that the radiation detector D has detected the second radiation R2, but instead of this, the embodiment and modified example of the embodiment may be configured to be applied to the radiation analysis apparatus 1 during performing the analysis. In this case, the radiation analysis apparatus 1 can correct the drift of the focus position during the analysis.

In addition, in the embodiment and the modified examples of the embodiment described above, as described above, a position of the point FP1 in the three-dimensional orthogonal coordinate system MC in the Z-axis direction matches with a position of the surface M2 in the Z-axis direction. In this case, the radiation analysis apparatus 1 can use information which is provided from the manufacturer (a maker or the like) of the radiation focusing unit 13 in advance and indicates the intensity distribution of the focus of the radiation focusing unit 13, as the first information. On the other hand, there may be a case where the user performs the analysis of the property or the structure of the object W by the radiation analysis apparatus 1, without matching a position of the point FP1 in the three-dimensional orthogonal coordinate system MC in the Z-axis direction with a position of the surface M2 in the Z-axis direction. In this case, it is preferable that the radiation analysis apparatus 1 uses information obtained by correcting, by the user, the information which is provided from the manufacturer (a maker or the like) of the radiation focusing unit 13 in advance and indicates the intensity distribution of the focus of the radiation focusing unit 13, as the first information. At this time, the user previously measures the reference intensity distribution by the radiation analysis apparatus 1 and corrects the information based on the measured result. Such correction may be performed by another method.

In addition, in the embodiment and the modified examples of the embodiment described above, as described above, positions of respective surfaces MM in the three-dimensional orthogonal coordinate system MC in the Z-axis direction are the same as one another. However, positions of respective surfaces MM in the three-dimensional orthogonal coordinate system MC in the Z-axis direction may be different from each other. In this case, the user previously measures the reference intensity distribution for each surface MM by the radiation analysis apparatus 1, corrects the information which is provided from the manufacturer (maker or the like) of the radiation focusing unit 13 in advance and indicates the intensity distribution of the focus of the radiation focusing unit 13. Then, the radiation analysis apparatus 1 uses the corrected information, as the first information. Such correction may be performed by another method.

As described above, the radiation analysis apparatus (in the example, the radiation analysis apparatus 1) according to the embodiment includes an excitation source unit (in the example, the excitation source unit 11) configured to irradiate an object (in the example, the object W), for which the radiation analysis apparatus analyzes property or a structure, with a first radiation (in the example, the first radiation R1), a radiation detection unit (in the example, the radiation detection unit 12) including three or more radiation detectors (in the example, the radiation detectors D) configured to detect a second radiation (in the example, the second radiation R2) generated from the object irradiated with the first radiation, a radiation focusing unit (in the example, the radiation focusing unit 13) disposed between the object and the radiation detection unit, and configured to focus the second radiation, a position changing unit (in the example, the position changing unit 14) configured to change a relative positional relationship between the radiation focusing unit and the radiation detection unit, and a control unit (in the example, the control unit 46) configured to control the position changing unit to change the positional relationship, based on first information which is stored in a storage unit (in the example, the storage unit 42) and indicates an intensity distribution of focus of the radiation focusing unit and second information which indicates a distribution based on a count that each of the radiation detectors has detected the second radiation. Accordingly, the radiation analysis apparatus can easily improve the detection efficiency of radiation.

In addition, in the radiation analysis apparatus, the first information is information indicating an intensity distribution of the second radiation emitted from the radiation focusing unit. Accordingly, the radiation analysis apparatus can easily improve the detection efficiency for the radiation, based on the first information indicating the intensity distribution of the second radiation emitted from the radiation focusing unit.

In addition, in the radiation analysis apparatus, the first information is information indicating the intensity distribution of the second radiation emitted from the radiation focusing unit, which is measured in advance, or the intensity distribution of the focus of the radiation focusing unit, which is the second radiation emitted from the radiation focusing unit, which is obtained by computer simulation. Accordingly, the radiation analysis apparatus can easily improve the detection efficiency for the radiation, based on the first information which is obtained by being measured in advance or by the computer simulation, and indicates the intensity distribution of the second radiation emitted from the radiation focusing unit, that is, of the focus of the radiation focusing unit.

In addition, in the radiation analysis apparatus, the first information is information indicating the intensity distribution of the radiation focusing unit, which is corrected by the user of the radiation analysis apparatus. Accordingly, the radiation analysis apparatus can easily improve the detection efficiency for the radiation, based on the first information that is information indicating the intensity distribution of the radiation focusing unit, which is corrected by the user.

In addition, in the radiation analysis apparatus, the first information is information indicating an intensity distribution in which each of the radiation detectors detects the second radiation with a high degree of the detection efficiency. Accordingly, the radiation analysis apparatus can easily improve the detection efficiency for the radiation, based on the first information that is information indicating the intensity distribution in which each of the radiation detectors detects the second radiation with a high degree of the detection efficiency.

In addition, in the radiation analysis apparatus, the first information is information indicating an intensity distribution in which each of the radiation detectors detects the second radiation with the highest degree of the detection efficiency. Accordingly, the radiation analysis apparatus can easily improve the detection efficiency for the radiation, based on the first information that is information indicating the intensity distribution in which each of the radiation detectors detects the second radiation with the highest degree of the detection efficiency.

In addition, in the radiation analysis apparatus, the radiation focusing unit is a capillary. Accordingly, the radiation analysis apparatus can suppress increasing the manufacturing costs for the radiation analysis apparatus, by changing the relative positional relationship between the radiation detection unit and the capillary based on the first information and the second information.

In addition, the radiation analysis apparatus calculates a count rate that each of the radiation detectors has detected the second radiation per unit time and calculates, as the second information, a distribution of a count rate calculated for each radiation detector. Accordingly, the radiation analysis apparatus can easily improve the detection efficiency for the radiation, based on the second information indicating a distribution of the count rate of each of the radiation detectors.

In addition, the radiation analysis apparatus controls the position changing unit to change the relative positional relationship between the radiation detection unit and the radiation focusing unit in a direction perpendicular to a surface on which the radiation detectors are arranged, based on a profile of a function representing the intensity distribution that the first information indicates and a profile of a function representing the distribution that the second information indicates. Accordingly, the radiation analysis apparatus can easily improve the detection efficiency for radiation, based on the profile of the function representing the intensity distribution that the first information indicates and the profile of the function representing the distribution that the second information indicates.

In addition, the radiation analysis apparatus controls the position changing unit to change the relative positional relationship between the radiation detection unit and the radiation focusing unit in a direction along a surface on which the radiation detectors are arranged, based on a peak of the intensity distribution that the first information indicates and a peak of the distribution that the second information indicates. Accordingly, the radiation analysis apparatus can easily improve the detection efficiency for radiation, based on the peak of the intensity distribution that the first information indicates and the peak of the distribution that the second information indicates.

Hereinabove, the embodiment of the present disclosure has been described in detail with reference to the drawings, but the specific configuration is not limited to this embodiment, and modifications, substitutions, deletions may be made without departing from the gist of the present disclosure.

In addition, a program for realizing the function of any of constituent parts in the above-described device (for example, the control device 20) is recorded on a computer-readable recording medium, and the program may be read and executed by a computer system. The "computer system" referred to here is regarded as including an operating system (OS) or hardware such as peripherals. In addition, the "computer-readable recording medium" refers to a portable medium such as a flexible disk, a magneto-optical disk, a ROM, and a compact-disk (CD)-ROM and a storage device such as a hard disk built in a computer system. Further, the "computer-readable recording medium" is regarded as including those holding programs for a certain period of time, such as a server when a program is transmitted via a network such as the Internet or a communication line such as a telephone line and a volatile memory (RAM) inside the computer system as a client.

In addition, the program may be transmitted from a computer system in which the program is stored in the storage device or the like to another computer system via a transmission medium or a transmission wave in the transmission medium. Here, the "transmission medium" transmitting a program refers to a medium having a function of transmitting information, such as a network (communication network) such as Internet and a communication channel (communication line) such as a telephone line.

In addition, the program may be for realizing some of the above-described functions. Further, the program may be a so-called differential file (differential program) which can realize the above-described function by being combined with programs already recorded in the computer system.

What is claimed is:

1. A radiation analysis apparatus that analyzes a property or a structure of an object, comprising:
   an excitation source configured to irradiate the object with a first radiation;
   a radiation detection unit including three or more radiation detectors configured to detect a second radiation generated from the object irradiated with the first radiation;
   a radiation focusing unit disposed between the object and the radiation detection unit, and configured to focus the second radiation;
   a position changing unit configured to manually or electrically change at least one of a position of the radiation detection unit with respect to the radiation focusing unit and a position of the radiation focusing unit with respect to the radiation detection unit to change a relative positional relationship between the radiation focusing unit and the radiation detection unit; and
   a drive control unit configured to drive the position changing unit to change the relative positional relationship, based on first information which is stored in a storage unit and indicates an intensity distribution of the second radiation emitted from the radiation focusing unit and second information which indicates a distribution based on a detection count of the second radiation detected by each of the radiation detectors.

2. The radiation analysis apparatus according to claim 1, wherein the first information is information indicating an intensity distribution of a focus of the radiation focusing unit.

3. The radiation analysis apparatus according to claim 1, wherein the first information is information indicating an intensity distribution corrected by a user of the radiation analysis apparatus, the information indicates an intensity distribution of a focus of the radiation focusing unit.

4. The radiation analysis apparatus according to claim 1, wherein the radiation focusing unit is a capillary.

5. The radiation analysis apparatus according to claim 1, wherein the drive control unit calculates a count rate of the second radiation detected per unit time by each of the radiation detectors, and calculates, as the second information, a distribution of the count rate calculated for each radiation detector.

6. The radiation analysis apparatus according to claim 1, wherein the drive control unit controls the position changing unit to change the relative positional relationship in a direction perpendicular to a surface on which the radiation detectors are arranged, based on a profile of a function representing the intensity distribution indicated by the first information and a profile of a function representing the distribution indicated by the second information.

7. The radiation analysis apparatus according to claim 1, wherein the drive control unit controls the position changing unit to change the relative positional relationship in a direction along a surface on which the radiation detectors are arranged, based on a peak of the intensity distribution indicated by the first information and a peak of the distribution indicated by the second information.

* * * * *